Feb. 16, 1965 H. KERRIGAN Plant Pat. 2,472
AZALEA PLANT
Filed Dec. 27, 1963
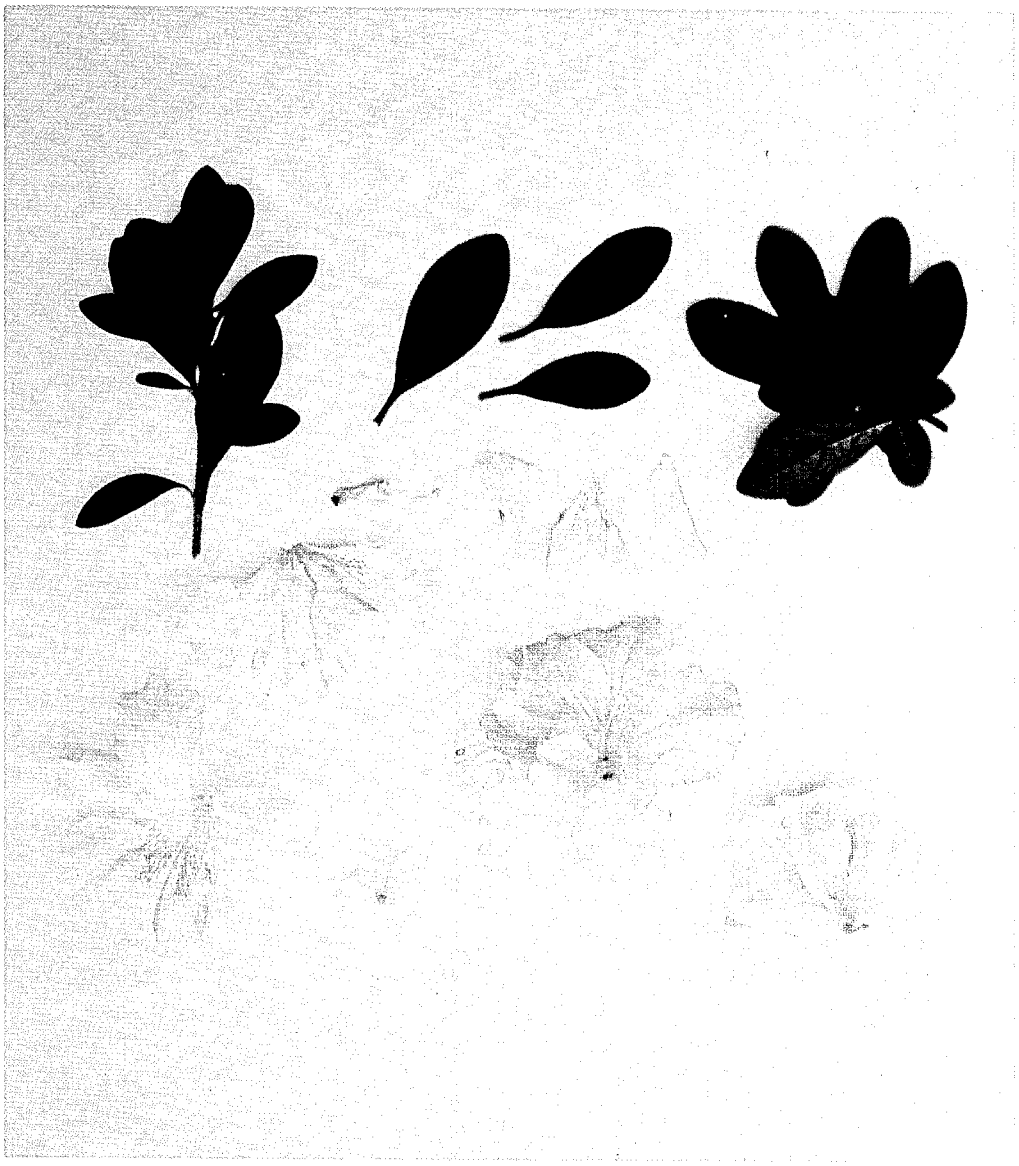

United States Patent Office

Plant Pat. 2,472
Patented Feb. 16, 1965

2,472
AZALEA PLANT

Howard Kerrigan, 3003 Totterdell St., Oakland, Calif.

Filed Dec. 27, 1963, Ser. No. 334,066
1 Claim. (Cl. Plt.—55)

This disclosure concerns a new and distinct variety of azalea of the florists' forcing type developed by me at Oakland, California, in 1948 as a direct result of a breeding program initiated by me in 1943 and carried out by me at Oakland, California.

The main objective of said breeding effort was the production of a new variety of florists' forcing azalea possessing the large flowers of the Belgian Indica type of forcing azalea with the profuse flowering and vigorous growth of the Sanders hybrids, particularly those varieties of the Sanders hybrids exhibiting the exceptional floriferousness of the Kurume type.

This result was achieved by crossing the Belgian Indica azalea "Paul Schäme," the seed parent with the Sanders hybrid "Loraine," the pollen parent, both unpatented.

My new variety is characterized by a number of new and distinct characters which make a particularly useful forcing azalea. In addition to the combination of the large flowers of the Belgian Indica types with the color, floriferousness, and vigor of the Sanders hybrids my new variety is also an exceptionally strong growing plant which produces an early and abundant bud set and a plant that may be forced very early and over a long period. Moreover, the flower color is unique. The ground color is white overlain with radial splashes of several intensities of pink of variable size and shape which give the general color effect of peppermint candy. My new variety is also a free branching, densely compact plant that develops a "florists' type head" with minimum pinching. Finally, the foliage is larger than azaleas of the Sanders type. My new variety also strikes roots readily.

All of these characteristics have remained constant during a number of asexual sequential generations of plants propagated by me from own root cuttings at Oakland, California, beginning in 1956.

The accompanying drawings disclose the details of my new invention and illustrate its distinctive horticultural features such as may be disclosed in this manner, essentially as they appear in nature and as accurately as current methods permit.

The following are detailed horticultural and botanical descriptions of my new azalea plant. The color designations are those employed in the Horticultural Colour Chart issued by Wilson Colour Ltd. in collaboration with the Royal Horticultural Society.

*Horticultural Description*

Low, spreading, bushy, compact plant with greenish stems moderately pubescent when young. The pubescence is light brown and typical in shape and size for this type of azalea. The leaves tend to be of two size classes, some averaging about 1½ inches long by ½ inch wide while others average about 2½ inches long by ¾ inch wide. The leaves are Ivy Green (HCC 0001060/3) above and Spinach Green (HCC 0960/3) below. The leaf margin is ciliate, the apex is only weakly bluntly pointed. The pubescence of the leaf is sparse, light brown or tan and obvious because of the contrast which the hairs present with the ground color of the leaf.

The individual inflorescence bears from 3–4 flowers. The flowers themselves are hose-in-hose and double with most of the stamens modified into a third inner hose as well as a number of free petaloids. The flower is spashed China Rose (HCC 024/2 and 024/1), much like the variegated roses, Careless Love (Plant Pat. 1,582) and Candy Stripe (Plant Pat. 2,278).

*Botanical description*

Low growing, spreading, heavily branched shrub to 30 inches high by 36 inches wide. The stems greenish when young, sparsely strigose, the hairs light brown or tan. Leaves large, varying widely in size, ranging from 1½ inches to 2½ inches long by ½ inch to ¾ inch wide. The leaves are barely obovate, petiolate, the petioles ranging in length from ⅛ inch to ⅜ inch long. The blades are dark green above, shiny, with sparse, tan, conspicuous, flattened hairs, and light green and glaucous below and bearing sparse, straw to near white pubescence on the interveinal epidermis and tan strigae on the prominent midrib. The pubescence of the lower leaf surface is concentrated along the veins. The leaf apex is somewhat truncated and submucronate.

The inflorescence bud shows 6–8 scales which are green and moderately pubescent. Each inflorescence bears from 3–4 flowers.

The pedicel is about ¼ inch long, densely pubescent, with white wooly hairs. The calyx is corolliform, imperfectly developed, deeply and unevenly indented and lobed. Considerable unconverted calyx tissue occurs, especially in the major sinuses separating the primary five limbs. The reverse of the calyx is moderately pubescent. The calyx is comparatively short, measuring ¾ inch deep by 1½ inches across.

The corolla is white, variously and irregularly splotched pink in several intensities of pigmentation, moderately flaring. The tube is ⅝ inch long and the corolla limbs are 1 inch long by 1½ inches wide, auriculate and with strongly undulate margins. The corolla measures 1¼ inches deep by 2⅝ inches across.

The stamens are few or none, mostly modified into a third partial hose and several free petaloids. The petaloids and lobes of the partial hose are about 1⅜ inches long by 1½ inches wide, extensively and deeply cut and indented.

The pistil is 1¼ inches long. The stigma is green, inconspiculously five lobed, and about twice as broad as the style. The style is 1 3/32 inches long, slender, 1/16 inch in diameter, green proximally and nearly white distally, only slightly curved and not at all sigmoid, so that the plane of the stigma is vertical and normal to the floral axis rather than horizontal. The ovary is ⅛ inch long, green, much darker than the base of the style, urseolate, necked, densely pubescent, the hairs white, wooly, hyaline.

Having disclosed my new invention in the above descriptions and the accompanying drawing, what I claim as new and patentable is:

A new and distinct variety of azalea plant of the florists' forcing type essentially intermediate between the Belgian Indica type of azalea and the Sanders hybrids, which is primarily characterized by its unique coloration, which is a white flower splashed with several tones of China Pink over the entire area of the flower; by its profuse and early bud set and its ease of forcing over an unusually long season; by its ease of propagation from own root cuttings and by its unusually rapid growth.

No references cited.

ABRAHAM G. STONE, *Primary Examiner.*